(12) United States Patent
    Sabir et al.

(10) Patent No.: US 8,978,234 B2
(45) Date of Patent: Mar. 17, 2015

(54) METHODS OF MANUFACTURING DEVICES FOR GENERATING SKIN GRAFTS

(75) Inventors: Sameer Ahmed Sabir, Cambridge, MA (US); Jeffrey Cerier, Cambridge, MA (US); Andrew Ziegler, Arlington, MA (US)

(73) Assignee: MoMelan Technologies, Inc., Cambridge, MA (US)

( * ) Notice: Subject to any disclaimer, the term of this patent is extended or adjusted under 35 U.S.C. 154(b) by 124 days.

(21) Appl. No.: 13/346,329

(22) Filed: Jan. 9, 2012

(65) Prior Publication Data

US 2013/0145596 A1    Jun. 13, 2013

Related U.S. Application Data

(60) Provisional application No. 61/567,946, filed on Dec. 7, 2011.

(51) Int. Cl.
    *B29C 65/00*    (2006.01)
    *B21D 39/03*    (2006.01)
    (Continued)

(52) U.S. Cl.
    USPC .............. 29/525.14; 29/428; 29/458; 29/525; 29/525.01; 29/525.13; 29/527.1; 606/132; 156/60

(58) Field of Classification Search
    CPC .... C04B 35/83; B32B 15/08; B60C 23/0493; B65C 9/265; B29C 70/08; A61B 2017/320004; A61B 17/54; A61B 17/545; A61B 17/322; A61B 2017/3225; A61B 2017/00747; A61B 17/50; A61B 17/3211; A61B 2017/32113; A61B 17/320758; A61B 17/320068; A61B 17/32002; A61B 17/1695; A61B 17/3201; A61B 10/00; A61B 2017/00761; A61B 17/06066; A61B 17/00526; A61I 27/60; A61F 9/013; A61F 9/0133; A61F 2/14; A61F 2/142; A61F 9/007; A61F 9/00763; A61F 2002/91533; A61F 2002/91541; B21D 53/88; B21D 39/04; B23P 15/00; B23P 11/02; B23P 19/001; B23P 19/10; B23P 2700/01; B23P 13/02; B21J 15/14; B21J 15/142; B21J 15/025; A47B 2230/0059; A63B 53/0466; A63B 53/0475; A63B 2053/0408; B21C 37/151; A01D 34/62; A61N 1/36; A61N 1/36007; A61N 1/36014; B21G 1/00; B29K 2021/00; E21B 19/16

USPC ......... 29/428, 453, 458, 525, 525.01, 525.13, 29/525.14, 527.1, 557, 558; 156/60; 606/132, 166, 131, 159, 161, 167–174

See application file for complete search history.

(56) References Cited

U.S. PATENT DOCUMENTS 2,379,574 A    7/1945  Goldthwait
3,054,404 A    9/1962  Meek
(Continued)

FOREIGN PATENT DOCUMENTS

EP    1614404 A2    1/2006
WO    9211879 A1    7/1992
(Continued)

OTHER PUBLICATIONS

Balaji, et al. "Isolation of a Novel Population of Multipotent Stem Cells From Epidermal Layer of Human Skin", Biology and Medicine, 2 (2): 57-67, (2010).
(Continued)

*Primary Examiner* — Essama Omgba
*Assistant Examiner* — Darrell C Ford
(74) *Attorney, Agent, or Firm* — Reza Mollaaghababa; Thomas J. Engellenner; Pepper Hamilton LLP

(57) ABSTRACT

The invention generally relates to methods for manufacturing components for use in a device for generating substantially planar micrografts. The methods of the invention provide for the manufacture of substantially uniform components for a cutter contained within the device, the cutter configured to cut a blister in order to produce a substantially planar graft.

16 Claims, 9 Drawing Sheets

(51) Int. Cl.
*B23P 11/00* (2006.01)
*B23P 17/00* (2006.01)
*A61B 17/322* (2006.01)
*A61B 17/32* (2006.01)

(56) References Cited

U.S. PATENT DOCUMENTS

| | | | |
|---|---|---|---|
| 3,782,387 A | | 1/1974 | Falabella |
| 4,345,374 A | * | 8/1982 | Jacobson ............... 30/47 |
| 4,666,447 A | | 5/1987 | Smith |
| 4,679,324 A | * | 7/1987 | Kirk ............... 30/346.58 |
| 4,773,418 A | * | 9/1988 | Hettich ............... 606/132 |
| 4,917,086 A | * | 4/1990 | Feltovich et al. ........... 606/132 |
| 5,015,584 A | | 5/1991 | Brysk |
| 5,386,633 A | * | 2/1995 | Kanno ............... 30/169 |
| 5,441,490 A | * | 8/1995 | Svedman ............... 604/289 |
| 5,460,939 A | | 10/1995 | Hansbrough |
| 5,476,478 A | | 12/1995 | Jackson |
| 5,489,304 A | | 2/1996 | Orgill |
| 5,496,339 A | * | 3/1996 | Koepnick ............... 606/166 |
| 5,545,222 A | | 8/1996 | Bonutti |
| 5,571,098 A | | 11/1996 | Domankevitz |
| 5,595,570 A | * | 1/1997 | Smith ............... 606/166 |
| 5,686,303 A | | 11/1997 | Korman |
| 5,730,717 A | | 3/1998 | Gelbfish |
| 5,759,193 A | | 6/1998 | Burbank |
| 5,817,115 A | * | 10/1998 | Nigam ............... 606/166 |
| 5,888,219 A | | 3/1999 | Bonutti |
| 5,914,261 A | | 6/1999 | Boulton et al. |
| 5,921,980 A | | 7/1999 | Kiru |
| 5,972,476 A | * | 10/1999 | Field ............... 428/174 |
| 5,976,163 A | * | 11/1999 | Nigam ............... 606/166 |
| 6,056,738 A | | 5/2000 | Marchitto |
| 6,063,094 A | | 5/2000 | Rosenberg |
| 6,071,247 A | | 6/2000 | Kennedy |
| 6,080,166 A | * | 6/2000 | McEwen et al. ........... 606/132 |
| 6,248,114 B1 | | 6/2001 | Ysebaert |
| 6,254,580 B1 | | 7/2001 | Svedman |
| 6,358,260 B1 | | 3/2002 | Ross |
| 6,364,908 B1 | | 4/2002 | Ysebaert |
| 6,402,770 B1 | | 6/2002 | Jessen |
| 6,436,078 B1 | | 8/2002 | Svedman et al. |
| 6,585,939 B1 | * | 7/2003 | Dapprich ............... 422/503 |
| 6,623,498 B1 | | 9/2003 | Ziemer |
| 6,800,282 B1 | | 10/2004 | Thomson |
| 6,860,904 B2 | | 3/2005 | Bonutti |
| 7,056,327 B2 | * | 6/2006 | Levesque et al. ........... 606/166 |
| 7,078,582 B2 | | 7/2006 | Stebbings |
| 7,137,979 B2 | | 11/2006 | Conrad et al. |
| 7,207,998 B2 | * | 4/2007 | Feingold ............... 606/166 |
| 7,208,006 B2 | | 4/2007 | Fleischman |
| 7,244,444 B2 | | 7/2007 | Bates |
| 7,540,875 B2 | | 6/2009 | Jessen |
| 7,625,384 B2 | | 12/2009 | Eriksson |
| 7,651,507 B2 | | 1/2010 | Mishra |
| 7,666,134 B2 | | 2/2010 | Eriksson |
| 7,666,192 B2 | | 2/2010 | Seegert |
| 7,708,746 B2 | | 5/2010 | Eriksson |
| 7,926,401 B2 | | 4/2011 | Mishra |
| 8,002,779 B2 | * | 8/2011 | Barker et al. ........... 606/132 |
| 8,109,187 B2 | | 2/2012 | Mishra |
| 8,162,957 B2 | | 4/2012 | Mishra |
| 8,187,285 B2 | | 5/2012 | Eriksson |
| 8,562,626 B2 | | 10/2013 | Sabir |
| 2001/0029380 A1 | | 10/2001 | Ysebaert |
| 2002/0052614 A1 | * | 5/2002 | GeBauer ............... 606/166 |
| 2003/0009185 A1 | | 1/2003 | Jessen |
| 2004/0097967 A1 | | 5/2004 | Ignon |
| 2004/0172045 A1 | | 9/2004 | Eriksson |
| 2004/0186498 A1 | * | 9/2004 | Barnes et al. ........... 606/167 |
| 2004/0215217 A1 | | 10/2004 | Banbury |
| 2004/0225309 A1 | * | 11/2004 | Eriksson et al. ........... 606/167 |
| 2004/0230215 A1 | | 11/2004 | Eriksson |
| 2004/0237744 A1 | | 12/2004 | Lin |
| 2005/0038520 A1 | | 2/2005 | Binette |
| 2005/0101972 A1 | | 5/2005 | Bhatavadekar |
| 2005/0221276 A1 | * | 10/2005 | Rozakis et al. ............... 435/4 |
| 2005/0234485 A1 | | 10/2005 | Seegert |
| 2006/0141616 A1 | | 6/2006 | Guu |
| 2006/0271070 A1 | | 11/2006 | Eriksson |
| 2007/0183974 A1 | | 8/2007 | Pearlman |
| 2009/0085286 A1 | * | 4/2009 | Grist et al. ............... 273/121 D |
| 2010/0012311 A1 | | 1/2010 | Colongo |
| 2010/0042127 A1 | | 2/2010 | Eriksson |
| 2010/0145360 A1 | | 6/2010 | Eriksson |
| 2010/0152651 A1 | * | 6/2010 | Boyden et al. ............... 604/66 |
| 2010/0152750 A1 | | 6/2010 | Memar |
| 2010/0310823 A1 | * | 12/2010 | Albertelli et al. ........... 428/139 |
| 2011/0077664 A1 | | 3/2011 | Schulz |
| 2011/0251602 A1 | | 10/2011 | Anderson |
| 2011/0264115 A1 | * | 10/2011 | Asrani et al. ............... 606/132 |
| 2012/0021186 A1 | * | 1/2012 | Schneider ............... 428/189 |
| 2012/0035599 A1 | | 2/2012 | Sabir |
| 2012/0035618 A1 | | 2/2012 | Sabir |
| 2012/0035619 A1 | | 2/2012 | Sabir |
| 2012/0035620 A1 | | 2/2012 | Sabir |
| 2012/0041430 A1 | | 2/2012 | Anderson |
| 2012/0125798 A1 | | 5/2012 | Baecker et al. |
| 2012/0172894 A1 | | 7/2012 | Sabir |
| 2012/0197267 A1 | | 8/2012 | Sabir |
| 2012/0201755 A1 | * | 8/2012 | Rozakis et al. ............... 424/9.1 |
| 2012/0201793 A1 | | 8/2012 | Bellomo |
| 2012/0244623 A1 | * | 9/2012 | Patel ............... 436/2 |
| 2012/0271320 A1 | | 10/2012 | Hall |
| 2013/0041385 A1 | | 2/2013 | Giovannoli |

FOREIGN PATENT DOCUMENTS

| | | |
|---|---|---|
| WO | 9528886 A1 | 11/1995 |
| WO | 9618432 A1 | 6/1996 |
| WO | 9633768 A2 | 10/1996 |
| WO | 9720509 A2 | 6/1997 |
| WO | 9816158 A1 | 4/1998 |
| WO | 03020333 A2 | 3/2003 |
| WO | 03039382 A2 | 5/2003 |
| WO | 03049626 A1 | 6/2003 |
| WO | 03049783 A2 | 6/2003 |
| WO | 2004071313 A2 | 8/2004 |
| WO | 2004075764 A1 | 9/2004 |
| WO | 2004078032 A2 | 9/2004 |
| WO | 2004105576 A2 | 12/2004 |
| WO | 2005033273 A2 | 4/2005 |
| WO | 2005046428 A2 | 5/2005 |
| WO | 2007117488 A2 | 10/2007 |
| WO | 2010036788 A2 | 4/2010 |
| WO | 2011038326 A1 | 3/2011 |
| WO | 2011059441 A1 | 5/2011 |
| WO | 2011075676 A2 | 6/2011 |
| WO | 2012019094 A2 | 2/2012 |
| WO | 2012019095 A2 | 2/2012 |
| WO | 2012019096 A1 | 2/2012 |
| WO | 2012019098 A1 | 2/2012 |
| WO | 2012102812 A1 | 8/2012 |
| WO | 2012145504 A1 | 10/2012 |

OTHER PUBLICATIONS

Sherif Shoukry Awad, "Chines Cupping: A Simple Method to Obtain Epithelial Grafts for the Management of REsistant Localized Vitiligo", American Society for Dermatologic Surgery, Inc.—Dermatol Surg, 34: 1186-1193 (2008).

Kreis et al., Expansion techniques for skin grafts: comparison between mesh and Meek island (sandwich-) grafts, Burns, (1994), 20(1):S39-S42.

Lari et al., Expansion technique for skin grafts (Meek technique) in the treatment of severely burned patients, Burns, (2001), 27:61-66.

Mulekar et al., Treatment of Vitiligo on Difficult-to-Treat Sites Using Autologous Noncultured Cellular Grafting, Dermatol Surg, (2009), 25(1):66-71.

Meek et al., Successful Microdermagrafting Using the Meek-Wall Microdermatome, Am J Surg, (1958), 96(4):557-558.

International Search Report and Written Opinion dated Dec. 16, 2011 for International Application No. PCT/US11/46737, 8 pages.

(56) References Cited

OTHER PUBLICATIONS

International Search Report and Written Opinion dated Dec. 16, 2011 for International Application No. PCT/US11/46738, 6 pages.
International Search Report and Written Opinion dated Dec. 23, 2011 for International Application No. PCT/US11/46739, 6 pages.
International Search Report and Written Opinion dated Dec. 6, 2011 for International Application No. PCT/US11/46741, 7 pages.

* cited by examiner

METHODS OF MANUFACTURING DEVICES FOR GENERATING SKIN GRAFTS

REFERENCE TO RELATED APPLICATIONS

This application claims the benefit of and priority to U.S. Provisional Application No. 61/567,946, filed Dec. 7, 2011, the contents of which are herein incorporated by reference in its entirety.

FIELD OF THE INVENTION

The invention generally relates to devices for generating and transferring substantially planar skin grafts.

BACKGROUND INFORMATION

Skin is the largest organ of the human body, representing approximately 16% of a person's total body weight. Because it interfaces with the environment, skin acts as an anatomical barrier to pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair skin damage. Traditional skin grafting is a surgical procedure in which a section of skin is removed from one area of a person's body (autograft), removed from another human source (allograft), or removed from another animal (xenograft), and transplanted to a recipient site of a patient, such as a wound site. As with any surgical procedure, skin grafting involves certain risks. Complications may include graft failure, rejection of the skin graft, infections at donor or recipient site, or autograft donor sites oozing fluid and blood as they heal. Certain of these complications (e.g., graft failure and rejection of the skin graft) may be mitigated by using an autograft instead of an allograft or a xenograft.

A problem encountered when using an autograft is that skin is taken from another area of a person's body to produce the graft, resulting in trauma and wound generation at the donor site. Generally, the size of the graft matches the size of the recipient site, and thus a large recipient site requires removal of a large section of skin from a donor site, leading to increased pain and discomfort and longer healing time. Additionally, as the size of the section of skin removed from the donor site increases, so does the possibility of infection.

Moreover, skin grafts are often difficult to obtain due to the tendency of the skin layer being cut to curl or fold over onto itself or the surgical instrument (e.g., dermatome), thereby comprising the integrity of the graft and making it unsuitable for use. This folding/curling tendency is particularly problematic the thinner the layer is that is being obtained, such as the epidermal layer.

While techniques have been developed for obtaining smaller micrografts that can be transferred onto a substrate for expansion prior to transplantation, such micrografts tend to clump together or can flip or fold during cutting, thereby comprising the integrity of the micrograft such that it will not properly grow on the substrate. As such, multiple cutting attempts are often necessary before a suitable, planar graft or micrograft is obtained, thereby producing multiple wound sites, leading to extreme discomfort, longer healing time, and a greater risk of infection.

SUMMARY

The invention provides methods for manufacturing components for use in devices for producing skin graft material. The invention provides manufacturing methods for creating plates, preferably metallic plates, for use in preparing skin grafts. Manufacturing methods as described herein are useful to fabricate plates for use in devices as described below.

Methods of the invention result in plates for use in harvesting skin grafts produced by the application of blistering to a donor site. Methods of the invention involve the generation of a plurality of plates having substantially planar mating surfaces from a material, preferably a metallic material. Preferably, at least one of the plates has substantially uniform thickness throughout the plate. In certain embodiments, each of the plurality of plates has a substantially uniform thickness throughout each plate and/or with respect to each other. The plurality of plates can be generated from the same material, or different materials.

A plurality of coupling members for coupling the plurality of plates together in a stacked configuration are preferably generated from the same material as at least one or more of the plate members such that the coupling members are substantially uniform in thickness with respect to each other and the at least one plate member, and contain substantially the same planar surface with respect to each other and the at least one of the plate member.

According to one aspect of the invention, a plurality plates are manufactured from the same sheet stock of material. For example, a single sheet stock of material is divided into a plurality of sections having uniform shape and size with respect to each other, each section corresponding to an individual plate member. At least one opening (e.g. hole or slot) is formed in each of the plate members such that the openings are in concentric alignment when the plate members are assembled in a stacked configuration.

In certain embodiments, the plurality of coupling members for coupling the plate members together in a stacked configuration are also formed from the same sheet stock from which the plate members are generated. Fabrication of the coupling members does not substantially change the planar surface of the plates, such that the plates are stackable in a form-fitting manner and subsequently movable with respect to one another. The coupling members are disposed between the plate members. The coupling members can be disposed along the outer surface of the plate members, or between one or more openings (e.g., holes or slots) formed within each plate. In certain aspects, the coupling members form a frangible section between the plates that is broken upon movement of the plates with respect to each other in operation, as described below. Optionally, a portion of the plate material at or around the site of the coupling is removed to accommodate at least a portion of the coupling member and forming a depression at or around the frangible section.

Preferred methods for fabricating plates for use in skin graft generator devices involve obtaining one or more plates of substantially uniform thickness and forming holes in the plates that align upon stacking. Plates preferably have integrated coupling members that do not substantially alter the thickness of the plates and allow for coupling of the plates via a frangible linkage. In operation, the plates are moved in order to break the coupling and to cut a graft from a skin blister formed by the device into which the plates are placed. Preferably, there are three plates, with a central plate having openings (e.g., holes or slots) that form a cutting surface. In operation, the plates are moved such that the cutting surface interacts with blisters protruding through aligned openings in a plate below. Ideally, coupling members are substantially uniform in shape and size and the frangible linkage is laser welded, but may also be a mechanical stamp, a mechanical punch, a weld, epoxy or other adhesive, formed via mechanical compression, snap fit, tongue and groove, post and bar, frangible pin or other known connectors.

Plates manufactured as described herein are useful in a device for reliably generating skin micrografts in a single attempt. A device of the invention is configured to generate a plurality of substantially planar micrografts in a single cutting motion. Devices of the invention are further capable of simultaneously transferring generated micrografts onto a substrate. Devices of the invention are particularly well-suited for generating and transferring a plurality of substantially planar epidermal micrografts.

In certain aspects, the invention provides a device that includes a body having a bottom surface configured for placement on skin, a mechanism for raising at least one blister on the skin, and a cutter configured to cut formed blisters in order to produce grafts for transplantation.

The cutter may include a plurality of plates, each plate having an array of openings (e.g., an array of holes or slots). In certain embodiments the openings are substantially cylindrical in shape. The openings in the arrays are of a size to facilitate production of a plurality of grafts from formed blisters. The openings can range in size from about 1 mm to about 12 mm diameter. In a particular embodiment, the openings are no greater than about 2 mm in diameter.

At least one of the plates is movable relative to the other plates. The plurality of plates in the cutter are configured such that a substantially planar graft (i.e., one that is not curled, folded or clumped) is produced.

The mechanism for raising the at least one skin blister can be a vacuum source, a heat source (e.g., a light source or warm air), or a combination of both.

Once the blister(s) is generated, a removable substrate is applied to the blister simultaneously transfer/retain the blister upon cutting. The substrate can include an adhesive to facilitate attachment of the blister to the substrate.

The device of the invention may further include a strap for securely coupling the device against a skin surface such as the inner thigh or buttocks. The strap may be adjustable in size, or may be a fixed size. In certain embodiments, the strap is a belt/loop fastener. In other embodiments, the strap is a metal or plastic cuff configured to for attachment around the upper thigh.

In another aspect, the invention provides a device for obtaining a skin graft that includes a hollow body having a bottom surface configured for placement on skin, a mechanism for raising at least one blister, and a plurality of plates, each plate including an array of holes configured so as to maintain the integrity of a graft produced by cutting the raised blister.

In certain embodiments the openings in the hole array of each plate are substantially cylindrical in shape and are of a size to facilitate production of a substantially planar graft. For example, the holes can range in size from 1 mm to a 12 mm diameter, or any specific value in between such range. In a particular embodiment, the openings in the hole arrays are no greater than about 2 mm in diameter.

The mechanism for raising the at least one skin blister can be a vacuum source, a heat source (e.g., a light source or warm air), or a combination of both.

A substrate removably connected to the body of the device directly contacts the generated blister(s) such that upon cutting of the blister, the cut portion of skin is attached to the substrate. The substrate can include an adhesive to facilitate attachment of the blister to the substrate.

The device may further include a strap for securely coupling the device against a skin surface such as the inner thigh or buttocks. The strap may be adjustable in size, or may be a fixed size. In certain embodiments, the strap is a belt/loop fastener. In other embodiments, the strap is a metal or plastic cuff configured to for attachment around the upper thigh.

In yet another aspect, the invention provides a cutting device that includes a first plate having at least one opening, a second plate having at least one opening, the second plate being attached to said first plate, and a third plate having at least one opening, the third plate being attached to said second plate. At least one of the plates is movable with respect to the other plates. For example, the second plate may be movable with respect to the first and/or third plates. In other embodiments, the third plate may be stationary in operation with respect to at least one of said first and second plates. In certain embodiments, the second plate is attached to said first plate via at least one frangible section. The frangible section is broken upon movement of said plates with respect to each other. The frangible coupling of the plate members to each other can be accomplished using a mechanical stamping technique, a mechanical punch technique, spot welding, an epoxy, an adhesive, mechanical compression, a snap-fit assembly, a tongue and groove assembly, a post and bar assembly, a frangible pin, or any combination thereof.

At least one of the openings in the first, second or third plate defines a cutting surface. In certain embodiments, the cutting surface on one of the plates engages a cutting surface on at least one other of said plates in operation (i.e., when at least one of the plates is moved with respect to the other plates). In certain embodiments, the opening in at least one of the plates moves with respect to the openings in at least another of said plates, thereby to perform a cutting action.

In certain embodiments, the first, second and third plates each include a plurality of openings that are concentrically aligned with respect to each other in a home position, and offset with respect to each other in an operating position (i.e., when at least one of the plates moves respect to the other plates).

These and other aspects of the devices of the invention are described in the figures, description and claims that follow.

DETAILED DESCRIPTION

Figure 1:
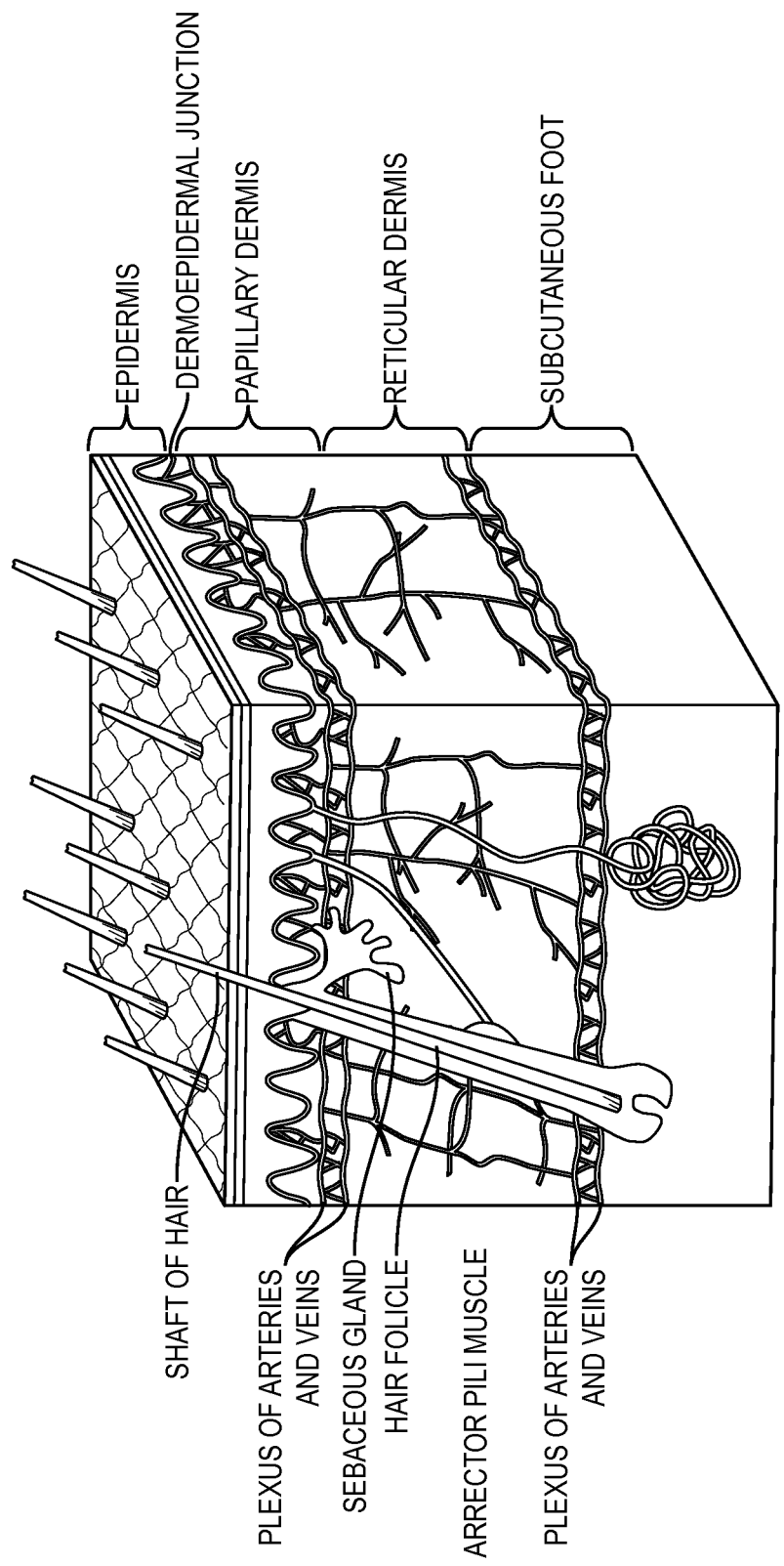
FIG. 1 is a drawing showing the anatomy of skin.

The skin consists of 2 layers. The outer layer, or epidermis, is derived from ectoderm, and the thicker inner layer, or dermis, is derived from mesoderm. The epidermis constitutes about 5% of the skin, and the remaining 95% is dermis. FIG. 1 provides a diagram showing the anatomy of skin. The skin varies in thickness depending on anatomic location, gender, and age of the individual. The epidermis, the more external of the two layers, is a stratified squamous epithelium consisting primarily of melanocytes and keratinocytes in progressive stages of differentiation from deeper to more superficial layers. The epidermis has no blood vessels; thus, it must receive nutrients by diffusion from the underlying dermis through the basement membrane, which separates the two layers.

Recently, research has shown that pluripotent stem cells are also located in the epidermal layer (Balaji et al., Biology and Medicine, 2(2): 57-67 (2010)). Epidermal grafting has been demonstrated in the literature to have significant applications in a number of different indications, including wound-care and vitiligo. However, epidermal grafting is difficult to perform in practice due to the extreme thinness (100 microns) and wet consistency of the tissue, as well as concerns regarding donor-site morbidity.

The dermis is a more complex structure. It is composed of 2 layers, the more superficial papillary dermis and the deeper reticular dermis. The papillary dermis is thinner, including loose connective tissue that contains capillaries, elastic fibers, reticular fibers, and some collagen. The reticular dermis includes a thicker layer of dense connective tissue containing larger blood vessels, closely interlaced elastic fibers, and coarse, branching collagen fibers arranged in layers parallel to the surface. The reticular layer also contains fibroblasts, mast cells, nerve endings, lymphatics, and some epidermal appendages. Surrounding the components of the dermis is the gel-like ground substance composed of mucopolysaccharides (primarily hyaluronic acid), chondroitin sulfates, and glycoproteins.

In a graft, the characteristics of the donor site that are more likely to be maintained after grafting to a recipient site is a function of the thickness of the dermal component of the graft. However, thicker grafts require more favorable conditions for survival due to the requirement for increased revascularization. It has been discovered, however, that a substantially epidermal graft according to the invention is more likely to adapt to the characteristics of the recipient site, presumably due to the presence of pluripotent stem cells in the epidermal layer.

Integrated Devices for Generating and Transferring Micrografts

In one aspect, the invention relates to an integrated device for generating micrografts and transferring micrografts. More specifically, the invention relates to a device for generating substantially planar micrografts and for preparing a surgical dressing to facilitate presentation of the micrografts to a patient in need thereof. The device of the invention can be used to prepare any type of skin graft, such as an epidermal skin graft, a split thickness graft, or a full thickness graft. However, the device of the invention is particularly well suited for preparing skin grafts including only or substantially only the epidermal layer of skin. The device of the invention can be used for autografts, allografts, or xenografts. In preferred embodiments, the grafts are autografts.

Figure 2A:
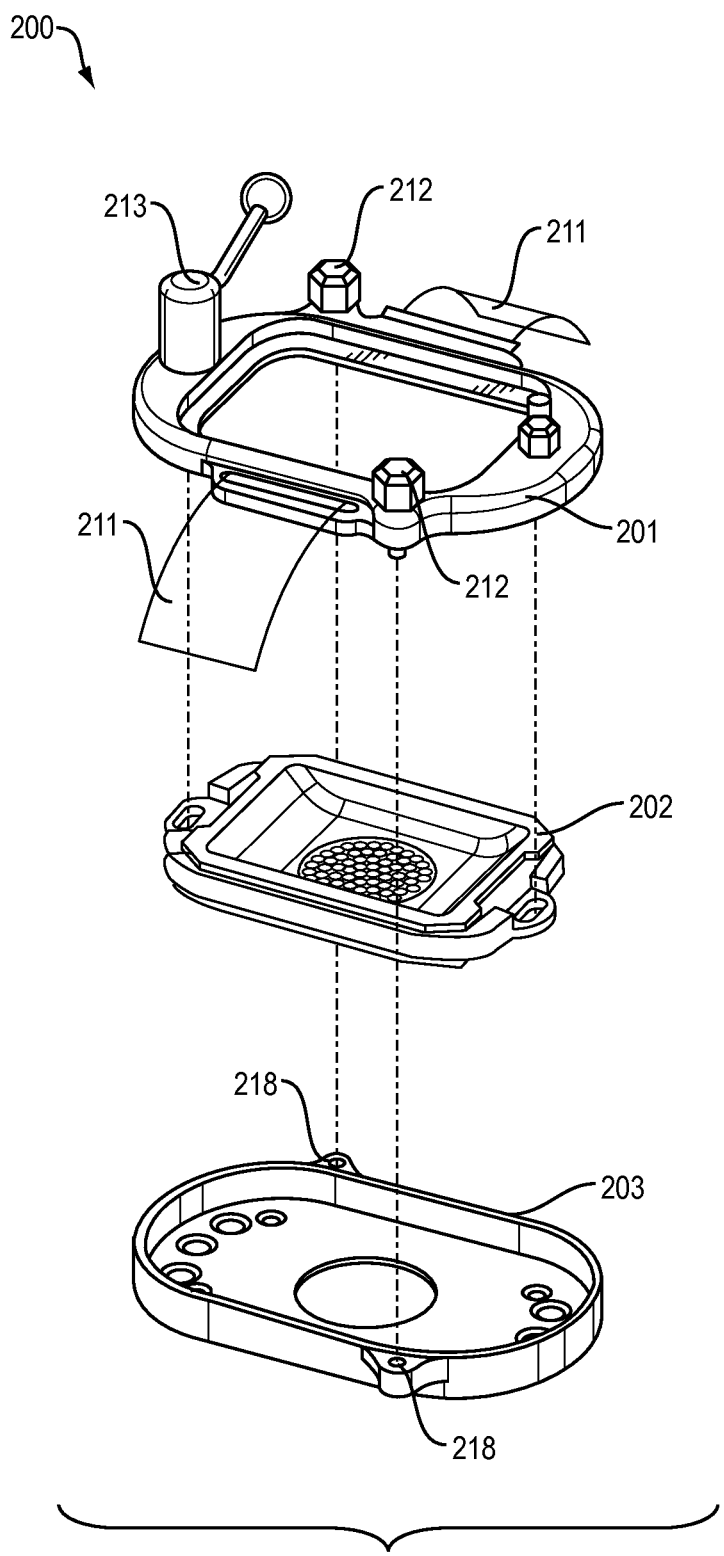
FIG. 2A is a schematic depicting the components of an exemplary embodiment of a blister harvesting device according to the invention.
Figure 2B:
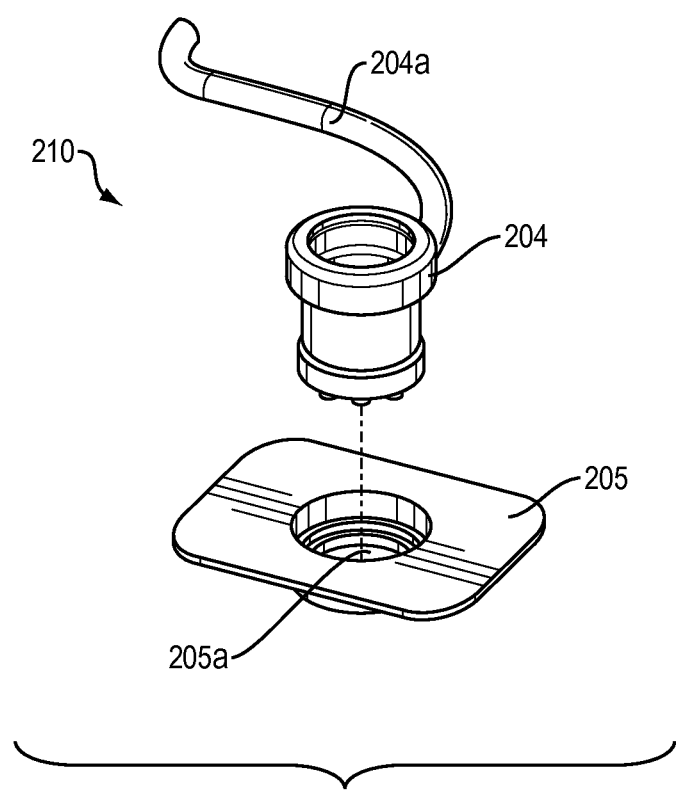
FIG. 2B is a schematic depicting the components of an exemplary embodiment of a blister generation module for coupling with the blister harvesting device of FIG. 2A.

Referring now to FIGS. 2A and 2B, device 200 includes a top housing 201, a cutter assembly 202 and a base housing 203. The top housing includes a rotatable handle 213 that is coupled to the cutter assembly 202. The top housing further includes a strap 211 for coupling the device 200 (once assembled) against a skin surface. The strap may be adjustable in size, or may be a fixed size. The top housing 201 is configured to removably receive a blister generation module 210 that includes a blister generation device 204 and an adaptor plate 205 (FIG. 2B).

Figure 3A:
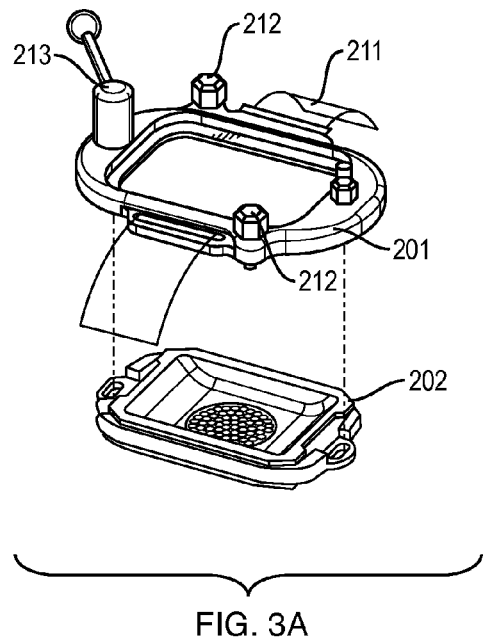
FIGS. 3A-3C are schematics depicting the assembly procedure of the components depicted in FIGS. 2A and 2B.
Figure 3B:
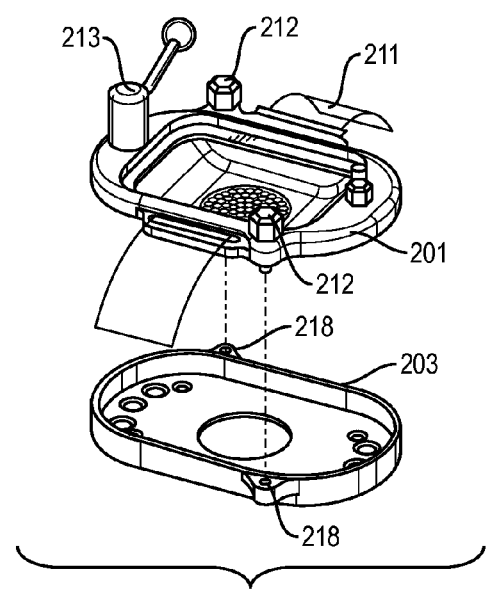
Figure 3C:
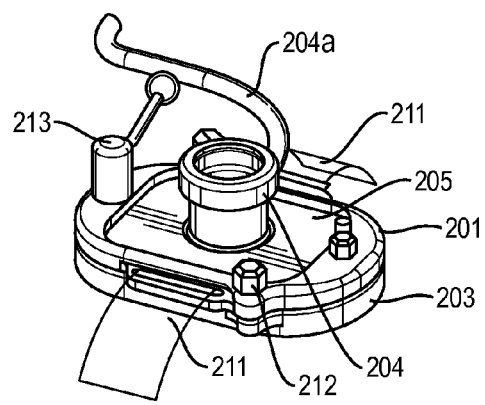

FIGS. 3A-3C depict the assembly of device 200. As shown in FIG. 3A, cutter assembly 202 is inserted into top housing 201. Top housing 201 is then coupled to base housing 203 via one or more threaded screws 212 that are received by a corresponding threaded holes 218 in base housing 203, such that cutter assembly 202 is disposed in between top housing 201 and bottom housing 203 (FIG. 3B). As shown in FIG. 3C, the blister generation module 210 is then inserted into top housing 201. In certain embodiments, the bottom of adaptor plate 205 that interfaces with top housing 201 includes a gasket around the bottom perimeter of the plate 205 to create an airtight seal between adaptor plate 205 and top housing 201 when coupled together. The blister generation device 204 of the blister generation module 210 is coupled to an opening 205a within adaptor plate 205. In certain embodiments, a gasket is disposed within opening 205a to form an airtight seal between blister generation device 204 and adaptor plate 205 when coupled together.

Figure 4:
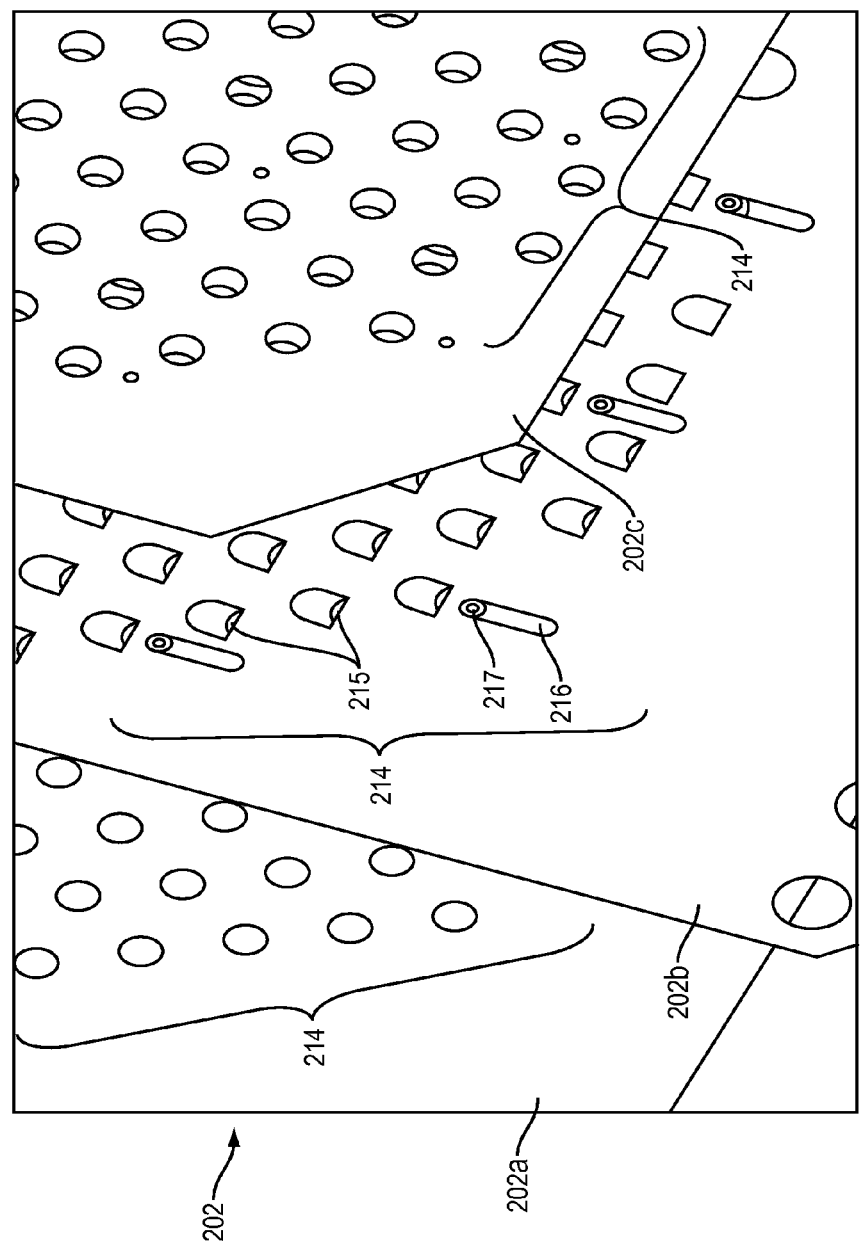
FIG. 4 is a schematic depicting the components of an exemplary embodiment of a cutter assembly for use in the devices according to the invention.

Referring now to FIG. 4, the cutter assembly 202 of device 200 is shown. The cutter assembly 202 includes a bottom plate 202a, a middle plate 202b, and a top plate 202c, each of which include an array of openings 214 (e.g., holes or slots) (sometimes referred to herein as hole array 214). One or more openings of the hole array 214 in the bottom 202a, middle 202b and/or top 202c plates define a cutting edge or surface 215. Preferably one or more openings in the hole array 214 of at least the middle plate 202b define a cutting edge or surface 215 (FIG. 4). The three plates are assembled in a stacked configuration with the middle plate 202b being coupled to the bottom plate 202a, and the top plate 202c being coupled to the middle plate 202b. One or more of plates 202a, 202b and 202c are configured to be movable in a lateral direction relative to each other. For example, the middle plate 202b may be laterally movable relative to the bottom plate 202a, the top plate 202c, or both. The top plate 202c may be movable relative to the middle plate 202b, the bottom plate 202a, or both. In certain embodiments, the one of more of plates 202a, 202b and 202c are configured to laterally move within a fixed distance relative to each other.

The middle plate 202b and/or top plate 202c can be coupled to their respective plates in the stacked configuration via at least one frangible section which serves to keep the plates in alignment until a lateral force is applied to the middle 202b and/or top 202c plate, which breaks the frangible section(s) and allows lateral movement of the plates relative to each other. In a particular embodiment, at least the middle plate 202b is coupled to the bottom plate 202a via at least one frangible section. The at least one frangible section is configured to break when a lateral force is applied to the middle plate 202b, allowing the middle plate 202b to move in a lateral direction relative to the bottom plate 202a, the top plate 202c, or both. Preferably, middle plate 202b is configured to laterally move within a fixed distance relative to the bottom plate 202a and/or top plate 202c. In a particular embodiment, the middle plate 202b includes one or more grooves or channels 216 that are configured to receive a pin 217 vertically extending from bottom plate 202a. Pin 217 is received at one end of channel 216 when the frangible section is intact, and laterally slides within channel 216 to the opposite end when the frangible section is broken, such that the lateral movement of plate 202b relative to plate 202a and/or 202c is fixed by the movement of pin 217 within channel 216.

One or more coupling members can be disposed between the plates to form the frangible sections, as described in further detail below. The one or more coupling members are disposed between the openings within hole array 214. Alternatively, the one or more coupling members are disposed between the plates outside of hole array 214. The frangible coupling of the plate members to each other can be accomplished using a mechanical stamping technique, a mechanical punch technique, spot welding, photo etching, an epoxy, an adhesive, mechanical compression, a snap-fit assembly, a tongue and groove assembly, a post and bar assembly, a frangible pin, or any combination thereof.

In certain embodiments, the middle plate 202b and/or top plate 202c can be coupled to their respective plates in the stacked configuration via at least one elastic member or spring member which serves to keep the plates in alignment until a lateral force is applied to the middle 202b and/or top 202c plate, which allows the elastic/spring section(s) to flex and allows lateral movement of the plates relative to each other. Upon removal of the lateral force, the elastic/spring sections relax, which allows the plates to return to their original positions such that the hole arrays 214 between the plates are once again in concentric alignment. The one or more elastic coupling members or spring members can be disposed between the openings within hole array 214. Alternatively, the one or more elastic coupling members or spring members can be disposed between the plates outside of hole array 214.

Preferably, the hole arrays 214 of the bottom 202a, middle 202b and top 202c plates include holes that are substantially similar in size and substantially cylindrical in shape. The size of the holes in each hole array 214 will depend on the size of the graft needed, with larger holes being used in each plate to produce larger grafts. In certain embodiments, the holes in the hole array 214 range between 1 mm and 12 mm in diameter, or any specific value in between. For example, the diameter of the holes in the hole array 214 of one or more of plates 202a, 202b and 202c can be 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm or 12 mm. In certain embodiments, the holes in hole array 214 vary in size and/or shape between the bottom plate 202a, middle plate 202b and/or top plate 202c. Once plates 202a, 202b and 202c of cutter assembly 202 are assembled (i.e., in the stacked configuration), the hole array 214 of each of plates 202a, 202b, and 202c are aligned. In a particular embodiment, hole arrays 214 of plates 202a, 202b, and 202c are concentrically aligned.

Figure 5A:
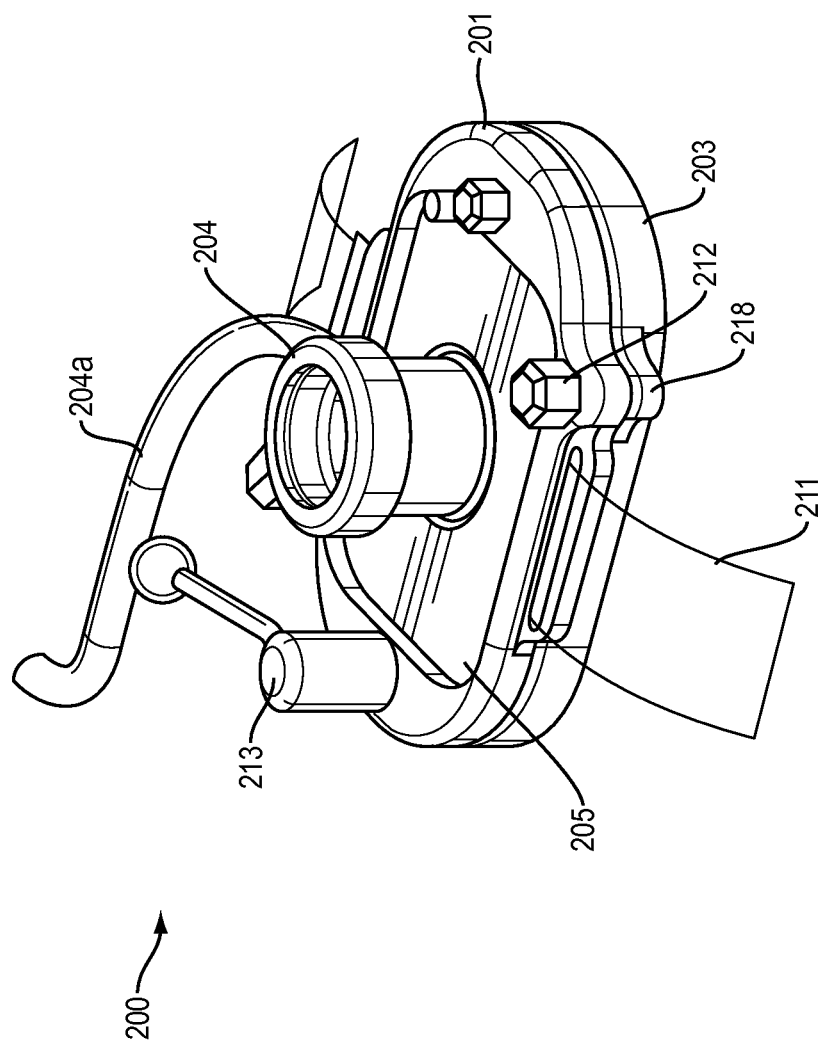
FIG. 5A is a schematic depicting an exemplary embodiment of a device according to the invention in a blister generation mode.
Figure 5B:
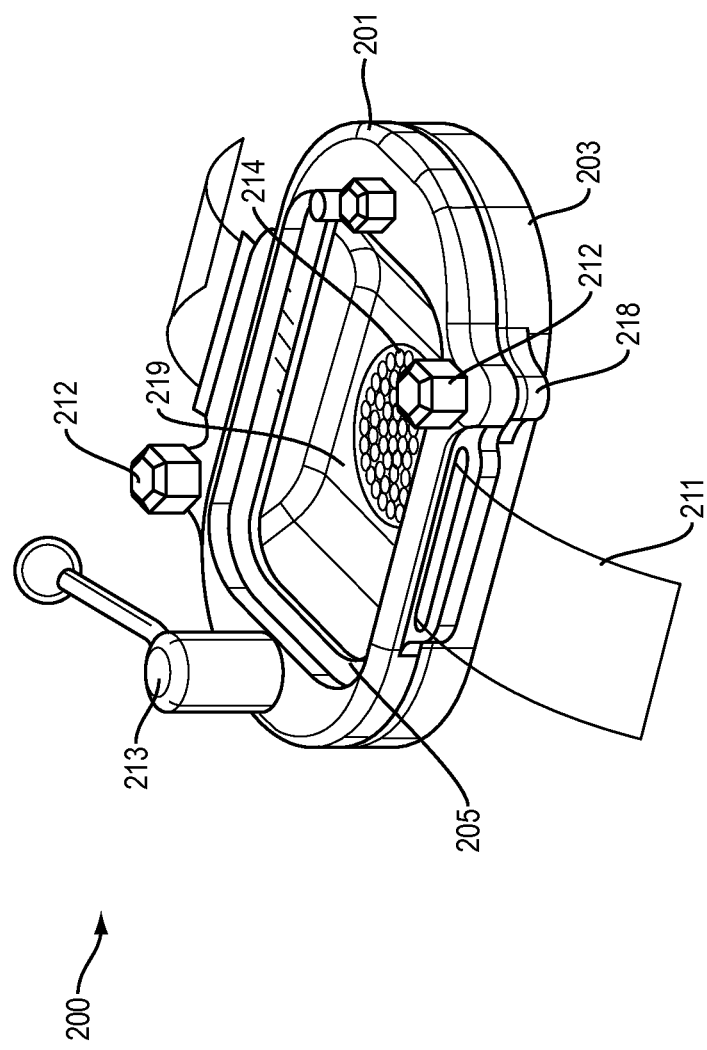
FIG. 5B is a schematic depicting an exemplary embodiment of a device according to the invention in a blister harvesting mode.
Figure 6A:
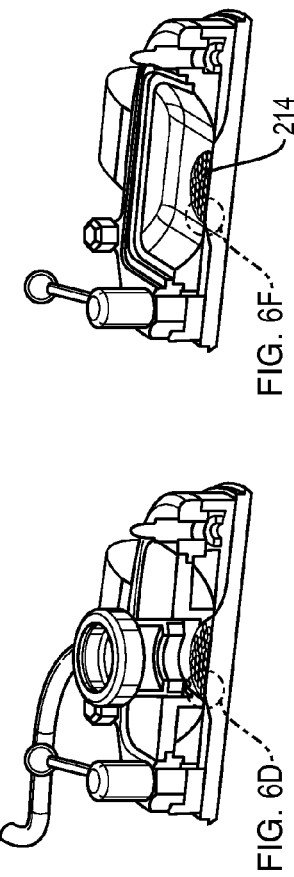
FIGS. 6A-6F are schematics depicting the blister generation steps using the device mode depicted in FIG. 5A.

The device 200 has two modes of operation: 1) a blister generation mode (FIG. 5A); and 2) a blister harvesting mode (FIG. 5B). As shown in FIG. 5A, the blister generation mode includes the assembly with the blister generation module 210. The blister generation module 210 is removed from the device assembly for blister harvesting mode (FIG. 5B). To produce and harvest a plurality of substantially planar micrografts, device 200 in the blister generation mode (i.e., with blister generation module 210, as shown in FIG. 5A), is placed on a donor site 220 such as an inner thigh of a patient (FIGS. 6A and 6B). Strap 211 is used to keep the device 200 in place against the skin surface of donor site 220. The blister generation device 204 is activated by turning/cranking handle 204a of blister generation device 204. The blister generation device 204 utilizes a vacuum component, a heating component, or a combination thereof, for raising skin blisters. An exemplary heating component is a light source. In a particular embodiment, mechanism is a combination of a vacuum component and a heating component.

In certain embodiments, the blister generation device 204 is a suction blister device for suction blister grafting. Suction blister grafting involves raising a skin blister, and then cutting off the raised blister. An exemplary suction blister grafting technique is shown in Awad, (Dermatol Surg, 34(9):1186-1193, 2008), the content of which is incorporated by reference herein in its entirety. This article also shows various devices used to form suction blisters. A suction blister device is also described in Kennedy et al. (U.S. Pat. No. 6,071,247), the content of which is incorporated by reference herein in its entirety. An exemplary device is the commercially available Negative Pressure Cutaneous Suction System from Electronic Diversities (Finksburg, Md.).

A device for raising a suction blister typically operates by use of suction chambers that are attached to a patient's skin. An instrument typically contains a power source, a vacuum pump, temperature controls and all related controls to operate multiple suction chambers. The suction chambers are connected to the console by a flexible connection. Each of the chambers is controlled by a preset temperature control to provide an optimal skin warming temperature. Both chambers share an adjustable common vacuum source that affects all chambers equally.

The chamber heating system provides a slight warming of an orifice plate of the device, which is in direct contact with the patient's skin surface. The negative pressure chamber is fabricated of mostly plastic components, with two removable threaded caps. The upper cap is fitted with a clear viewing lens so that the actual blister formation can be observed. The opposite end of the chamber is fitted with a removable orifice plate that is placed on the patient's skin. Since this plate is simply threaded onto the chamber end, multiple plates with different opening patterns can be interchanged as desired.

The interior of the device is warmed and illuminated by an array of low voltage incandescent lamps. This lamp array is controlled from the instrument console temperature controller, cycling as needed, to maintain the set point temperature. The heat from these lamps is radiated and conducted to the orifice plate, which then warms the patient's skin. The chamber is connected to the console via a composite vacuum and low voltage electrical system. Quick connections are used for the vacuum and electrical system to facilitate removal and storage.

The Negative Pressure Instrument console is a self-contained fan cooled unit which is designed to operate on 120 VAC 60 Hz power. Vacuum is supplied by an industrial quality diaphragm type vacuum pump, capable of a typical vacuum of 20 in Hg (0-65 kpa) at 0 CFM. An analog controller that is preset to 40° C. provides the temperature control for each suction chamber. This provides accurate control of the orifice plate temperature. The instrument console has internal adjustments that allow the user to recalibrate the temperature setting if desired. Other temperatures can be preset if desired. The front panel includes a vacuum gauge and vacuum bleeder adjustment to regulate the vacuum to both chambers. The console front panel also contains the connections for the chamber assemblies.

Figure 6C:
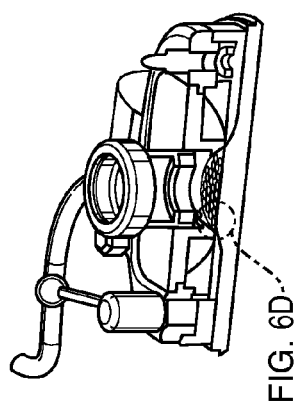
Figure 6E:
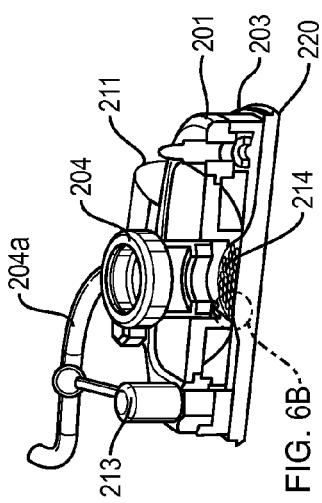
Figure 6B:
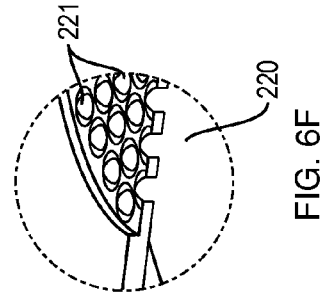
Figure 6D:
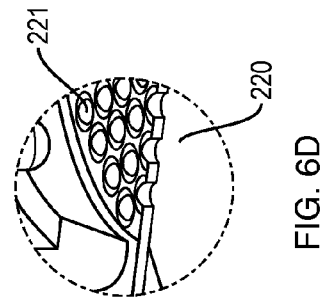
Figure 6F:
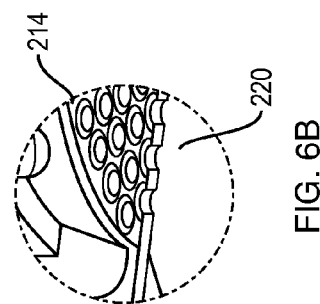

The application of a moderate negative pressure from the blister generation device 204 causes the patients skin to be gently drawn through the concentrically aligned hole arrays 214 of plates 202a, 202b and 202c in cutter assembly 202 (FIGS. 6C and 6D). Such action results in generation of a plurality of raised microblisters 221, particularly epidermal microblisters. The blisters 221 may or may not be fluid-filled. The plurality of suction blisters 221 generated are of uniform size, approximately the size of the openings/holes in the hole arrays 214 of the three plates of cutter assembly 202, and are uniformly spaced in accordance with the configuration of the holes in hole array 214, such that a plurality of substantially planar microblisters 221 are generated. The skin and blister area is generally not damaged and patient discomfort is minimal.

Figure 7A:
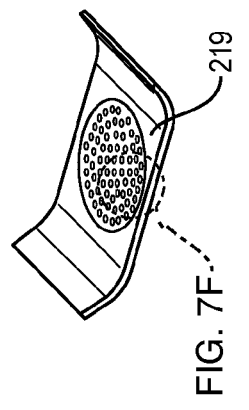
FIGS. 7A-7F are schematics depicting the blister harvesting steps using the device mode depicted in FIG. 5B.

Once the substantially planar microblisters 221 are raised/generated the device is converted into the blister harvesting mode by removing the blister generation module 210 from the top housing 201, thereby exposing the hole array 214 in the top plate 202c of cutter assembly 202. At least a portion of the raised microblisters 221 protrude through the top of the hole array 214, as shown in FIGS. 6B and 6C. A substrate 219 is applied to the surface of hole array 214, as shown in FIGS. 5B and 7A, such that the substrate 219 is in direct contact with the raised blisters 221.

Figure 7C:
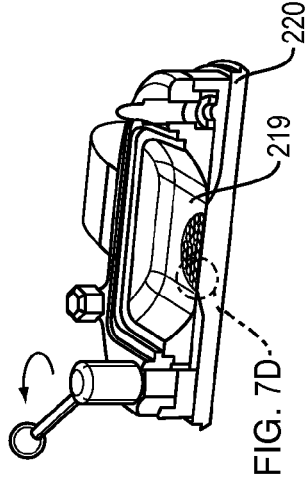
Figure 7E:
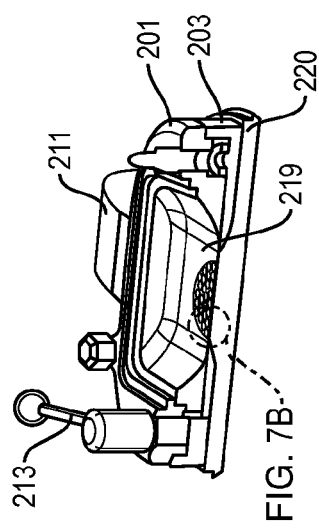
Figure 7B:
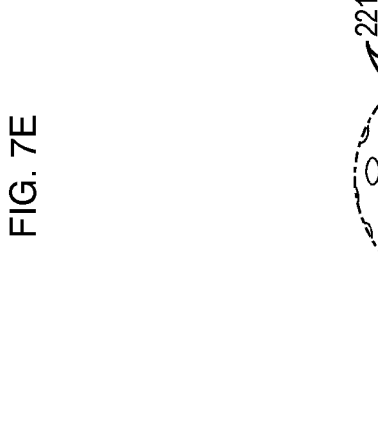
Figure 7D:
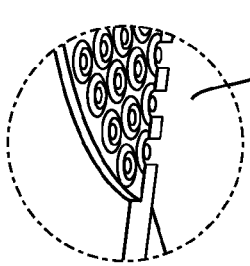
Figure 7F:
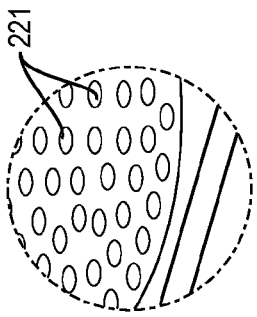

To cut the raised blisters 221, handle 213 is rotated in a clockwise or counterclockwise direction (FIG. 7C). Handle 213 is coupled to the middle plate 202b of cutter assembly 202 in a configuration that translates the rotational movement of the handle 213 into lateral movement of middle plate 202b. The lateral force applied to middle plate 202b by handle 213 causes middle plate 202b to move in a lateral direction relative to bottom plate 202a and/or top plate 202c, thereby disrupting the alignment of the hole arrays 214 between plates 202a, 202b and 202c. The lateral displacement of the hole array 214 of middle plate 202b causes the cutting surface 215 defined by one or more holes in the hole array 214 to cut the raised blisters 221. As the raised blisters 221 are cut, they are simultaneously transferred/retained on substrate 219 in the same configuration as generated within hole array 214, resulting in a substrate containing a plurality of micrografts that are uniformly spaced and oriented on the substrate 219 (i.e., a substrate containing a plurality of substantially planar micrografts).

Certain embodiments of device 200 integrate consumable/single-use components (e.g., substrate 219 and/or cutter assembly 202) and re-usable, sterilizable or cleaned components (e.g., top housing 201, base housing 203 and blister generation module 210), thereby providing a reliable system that is easy to maintain. All components of device 200 that come into contact with the donor and/or recipient tissue (both single-use and reusable components) must be sterile/sterilized to reduce the risk of infection.

In certain embodiments, substrate 219 includes an adhesive on one side that facilitates attachment of the blisters to the substrate. The substrate material may have intrinsic adhesive properties, or alternatively, a side of the substrate may be treated with an adhesive material, e.g., an adhesive spray such as LEUKOSPRAY (Beiersdoerf GmbH, Germany). The substrate may be a deformable non-resilient material. A deformable non-resilient material refers to a material that may be manipulated, e.g., stretched or expanded, from a first configuration to a second configuration, and once in the second configuration, there is no residual stress on the substrate. Such materials may be stretched to an expanded configuration without returning to their original size. Such deformable non-resilient materials tend to be soft, stiff or both soft and stiff. Softness is measured on the durometer scale. An example of such a material is a soft polyurethane. A soft polyurethane is produced is as follows. Polyurethanes in general usually have soft and hard segments. The hard segments are due to the presence of phenyl bridges. In a soft polyurethane, the phenyl bridge is switched out for an aliphatic, which is more flexible as its 6 carbon ring has no double bonds. Therefore, all the segments are soft. On the Durometer Scale, a soft polyethylene is rated about Shore 80A. Other materials suitable for use with the device 200 of the invention include low density polyethylene, linear low density polyethylene, polyester copolymers, polyamide copolymers, and certain silicones. In a particular embodiment, the substrate 219 is Tegaderm™, which is a transparent medical dressing manufactured by 3M Company, U.S.A.

Ultimately, the substrate containing the plurality of uniformly spaced and oriented (i.e., substantially planar) micrografts is applied to a recipient of site of a patient. Prior to applying the grafts to the recipient site, the site is prepared to receive the grafts using any technique known in the art. Necrotic, fibrotic or avascular tissue should be removed. The technique used to prepare the site will depend on damage to the recipient site. For example, epidermal tissue, if present at the recipient site, can be removed to prepare the area for receiving the micrografts. Burned or ulcerated sites may not need removal of epidermal tissue, although some cleaning of the site or other preparation of the site may be performed. Wounds should be debrided and then allowed to granulate for several days prior to applying the graft. Most of the granulation tissue should be removed since it has a tendency to harbor bacteria. Applying silver sulfadiazine to the wound for 10 days prior to grafting reduces the bacterial count greatly.

The size of the area at the recipient site can be about the same size as the area of the substrate having micrografts adhered thereto. This size generally will be greater than the area of the original graft tissue that was removed from the donor site to form the micrografts. The depigmented or damaged skin can be dermabraded with sandpaper or another rough material. Alternatively, the epidermal tissue can be removed from the recipient site by forming one or more blisters over the area to be treated, e.g., a suction blister or a freezing blister, and the raised epidermal blister tissue can then be removed by cutting or another procedure.

The substrate having the substantially planar micrografts can be placed over the area to be treated to form a dressing. A portion of the substrate having the micrografts can be positioned over the area to be repaired, e.g., the area from which the epidermal tissue has been abraded or removed for repigmentation. The substrate can be fixed in place over the treatment area, e.g., using tape or the like. The substrate can be removed after sufficient time has elapsed to allow attachment and growth of the micrografts in the treatment area, e.g., several days to a few weeks.

Manufacturing Uniform Components for Use in Integrated Devices of the Invention

The invention further relates to methods for manufacturing uniform components for use in the integrated devices of the invention.

In order to generate substantially planar micrografts, the components within cutter assembly 202 must be substantially uniform with respect to one another. In particular, the planar surfaces of the components within cutter assembly 202 must be substantially uniform.

In certain aspects one or more coupling members are used to create a frangible coupling between at least two of plate members 202a, 202b and 202c. The coupling members are disposed between two or more of the plate members to form a frangible section that is broken upon movement of said plates with respect to each other, as previously described. The tolerance for any inconsistencies between the planar surfaces of the coupling members and one or more of the plate members and/or inconsistent dimensions (e.g., width) between the coupling members and one or more of the plate members is very low and could result in non-planar, non-uniform micrografts and device malfunction.

Inconsistencies between the planar surfaces of different stocks of sheet material, manufacturing methods of blanks for the coupling members and/or plates, and finishing methods of the coupling members and/or plates can each increase tolerance stackups beyond an acceptable level, thereby decreasing the efficiency and function of device and resulting in micrografts that are unusable, and increase patient discomfort/distress.

The accumulated variations in production dimensions of the coupling members, variations in production dimensions of the plate members, and variation in the spacing between plate members, can each increase tolerance stackups and decrease device function. In order to optimize the tolerances within the cutter assembly 202, the plurality of coupling members are preferably formed from the same sheet stock of material as at least one plate member in the cutter assembly 202. In a particular embodiment, the plurality of coupling members and at least middle plate member 202b in cutter assembly 202 are preferably formed from the same sheet stock of material (e.g., a single sheet stock of material). Forming the coupling members and the middle plate member 202b from the same sheet stock ensures a uniform thickness between the coupling members and between the coupling members and plate member 202b, and ensures uniform, planar mating surfaces between the coupling members and plate member 202b, thereby decreasing tolerance stackups within cutter assembly 202 and ensuring proper device function.

Plate members 202a, 202b, and 202c can be formed from the same material, or different materials with respect to each other, so long as the materials used result in substantially planar mating surfaces between the three plates. Preferably, plate members 202a, 202b, and 202c are formed from a metallic material (e.g., the same metallic material, or different metallic materials).

In certain embodiments, each of plate member 202a, 202b, and 202c is formed from the same sheet stock of material, preferably a single sheet stock of material. One or more openings (e.g., holes or slots) are formed within each plate member to form hole arrays 214 that align when the plate members are assembled, as previously described. In certain embodiments, the coupling members are formed from the same sheet stock from which the plurality of plate members are generated. Forming the coupling members and plate members from the same sheet stock ensures uniformity in the thickness among and between the coupling members and plate members, and uniformly planar mating surfaces between the coupling members and plate members, thereby decreasing tolerance stackups within cutter assembly 202 and ensuring proper device function.

The coupling members can be any shape or dimension sufficient to couple the plates together without obstructing the holes in the hole arrays 214 through which the suction blisters are raised. For example, the coupling members can be substantially square or rectangular in shape. Alternatively, the coupling members are substantially circular in shape. In certain embodiments, the coupling members are of a sufficient shape and size for location between the holes of the hole arrays 214 of the plate members. In other embodiments, the coupling members are of a sufficient shape and size for location along the edges of the plurality of plates.

Any method can be used to manufacture the plates and/or coupling members, such as drilling, milling, laser etching, lithographic processing, photo etching, laser ablation and the like. In a particular embodiment, a photo etching process is used to manufacture the plates and/or coupling members.

The frangible coupling between the coupling members and plate members can be accomplished using a variety of techniques. For example, the coupling members can be frangibly coupled between the plate members via spot welding techniques (e.g., laser spot welding), via an adhesive such as epoxy, polyurethane, acrylic or a resin, via a frangible pin, a snap-fit or tongue and groove assembly. Such frangible coupling techniques can be accomplished using one or more manufacturing processes such as cold-heading, multiple-die forming, multiple-die progression, multiple-die headers, casting, stamping, punching, atomic hydrogen welding, bare metal arc welding, carbon arc welding, flux cored arc welding, gas metal arc welding, gas tungsten arc welding, plasma arc welding, shielded metal arc welding, submerged arc welding, air acetylene welding, oxyacetylene welding, oxygen/propane welding, oxy hydrogen welding, pressure gas welding, resistance spot welding, resistance seam welding, projection welding, flash welding, upset welding, co-extrusion welding, cold pressure welding, diffusion welding, explosion welding, electromagnetic pulse welding, forge welding, friction welding, friction stir welding, hot pressure welding, hot isostatic pressure welding, roll welding, ultrasonic welding, electron beam welding, electroslag welding, flow welding, induction welding, laser beam welding, percussion welding, thermite welding, electrogas welding, and stud arc welding.

Optionally, a portion of the plate material at or around the site of the frangible coupling is removed to accommodate at least a portion of the coupling member by forming a depression at or around the frangible section. For example, in one embodiment, laser etching or photo etching on the plate member is used to circumscribe the coupling point at or proximal to the frangible coupling. In another embodiment, a depression at or proximal to the plate member can be removed with any method known in the art, for example drilling, milling, laser etching, photo etching, laser ablation and the like.

Preparation of Dressings/Skin Grafts for Treating Damaged Skin

The devices of the invention can be used to prepare a skin graft to repair numerous different types of skin damage. For example, the devices of the invention may be used to prepare grafts to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

In particular embodiments, devices 200 of the invention are used to prepare a skin graft(s) for treating vitiligo. Vitiligo is a chronic disorder that causes depigmentation of patches of skin. It occurs when melanocytes, the cells responsible for skin pigmentation, die or are unable to function. Although patches are initially small, they often enlarge and change shape. When skin lesions occur, they are most prominent on the face, hands and wrists. Some lesions have hyper-pigmentation around the edges. Depigmentation is particularly noticeable around body orifices, such as the mouth, eyes, nostrils, genitalia and umbilicus.

Vitiligo is generally classified into two categories, non-segmental vitiligo and Segmental vitiligo. In non-segmental vitiligo (NSV), there is usually some form of symmetry in the location of the patches of depigmentation. New patches also appear over time and can be generalized over large portions of the body or localized to a particular area. Vitiligo where little pigmented skin remains is referred to as vitiligo universalis. Non-segmental vitiligo can come about at any age, unlike segmental vitiligo which is far more prevalent in teenage years.

Segmental vitiligo (SV) differs in appearance, aetiology and prevalence from associated illnesses. Its treatment is different from that of non-segmental vitiligo. It tends to affect areas of skin that are associated with dorsal roots from the spine. It spreads much more rapidly than non-segmental vitiligo and, without treatment, it is much more stable/static in course and not associated with auto-immune diseases.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for manufacturing a plurality of plates for use in a device for obtaining a skin graft, said method comprising the steps of:
   obtaining a plurality of plates,
   forming a plurality of openings in said plates such that the openings align upon stacking said plates; and
   forming a plurality of coupling members in at least one of said plates, wherein said coupling members create at least a frangible linkage between at least two of said plates whereby the openings of the at least two plates can be maintained in alignment prior to use,
   wherein said at least a frangible linkage is configured to break in response to application of a lateral force to at least one of said at least two plates to allow relative movement thereof.

2. The method of claim 1, wherein at least one of said one of more openings forms a cutting edge.

3. The method of claim 2, further comprising the step of attaching two or more plates together via said coupling members.

4. The method of claim 3, wherein one or more of said coupling members are disposed between at least two of said plates.

5. The method of claim 1, wherein said forming steps comprise laser etching, photo etching or lithographic processing.

6. The method of claim 5, wherein said frangible linkage is selected from a mechanical stamp, a mechanical punch, a weld, epoxy, an adhesive, mechanical compression, a snap-fit, a tongue and groove, a post and bar, or a frangible pin.

7. The method of claim 1, said coupling members are of substantially uniform shape and size.

8. The method of claim 1, further comprising the step of coupling two or more plates together via said coupling members.

9. The method of claim 1, further comprising removing a portion of material at or around a site of at least one of said coupling members to accommodate at least a portion of said coupling member.

10. The method of claim 9, wherein said plates are slidable with respect to each other upon breaking said frangible linkage.

11. The method of claim 1, wherein at least one of said plurality of plates comprises a substantially uniform thickness.

12. The method of claim 11, wherein said coupling members do not substantially alter said uniform thickness.

13. The method of claim 1, wherein said plurality of plates comprises a bottom plate, a middle plate and a top plate.

14. The method of claim 13, wherein said at least one frangible linkage couples said middle plate to any of said top and said bottom plate.

15. The method of claim 14, wherein upon breakage of said at least one frangible linkage the middle plate is configured to move relative to any of the top plate and the bottom plate within a fixed distance.

16. The method of claim 14, wherein said middle plate comprises any of at least a groove or a channel adapted to receive a pin vertically extending from the bottom plate, wherein the pin is received at one end of said groove or channel when said at least one frangible linkage is intact and is adapted to laterally slide to an opposite end of said groove or channel when said frangible linkage is broken.

* * * * *